United States Patent
Reschke (10) Patent No.: US 8,808,288 B2
(45) Date of Patent: Aug. 19, 2014

(54) SURGICAL FORCEPS INCLUDING BELT BLADE REVERSER MECHANISM

(75) Inventor: Arlen J. Reschke, Longmont, CO (US)

(73) Assignee: Covidien LP, Mansfield, MA (US)

( * ) Notice: Subject to any disclaimer, the term of this patent is extended or adjusted under 35 U.S.C. 154(b) by 962 days.

(21) Appl. No.: 12/719,407

(22) Filed: Mar. 8, 2010

(65) Prior Publication Data

US 2011/0218530 A1 Sep. 8, 2011

(51) Int. Cl.
*A61B 18/14* (2006.01)
*A61B 17/285* (2006.01)
*A61B 17/295* (2006.01)

(52) U.S. Cl.
USPC ............................................ 606/51; 606/205

(58) Field of Classification Search
CPC ........... A61B 18/1442; A61B 18/1445; A61B 2018/1442; A61B 2018/1452; A61B 2018/1455; A61B 17/282; A61B 17/285; A61B 17/29; A61B 17/295
USPC ................................ 606/41, 50–52, 205–207
See application file for complete search history.

(56) References Cited

U.S. PATENT DOCUMENTS

| | | | |
|---|---|---|---|
| 4,108,011 A * | 8/1978 | Gregg et al. | 474/153 |
| D263,020 S | 2/1982 | Rau, III | |
| D295,893 S | 5/1988 | Sharkany et al. | |
| D295,894 S | 5/1988 | Sharkany et al. | |
| 5,308,353 A | 5/1994 | Beurrier | |
| D348,930 S | 7/1994 | Olson | |
| 5,388,568 A * | 2/1995 | van der Heide | 600/146 |
| D384,413 S | 9/1997 | Zlock et al. | |
| 5,716,366 A | 2/1998 | Yates | |
| 5,792,165 A | 8/1998 | Klieman et al. | |
| 5,797,927 A | 8/1998 | Yoon | |
| 5,906,629 A * | 5/1999 | Oren et al. | 606/205 |
| 6,004,335 A | 12/1999 | Vaitekunas et al. | |
| D424,694 S | 5/2000 | Tetzlaff et al. | |
| D425,201 S | 5/2000 | Tetzlaff et al. | |
| D449,886 S | 10/2001 | Tetzlaff et al. | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 12/244,873, filed Oct. 3, 2008.

(Continued)

*Primary Examiner* — Ronald Hupczey, Jr.

(57) ABSTRACT

A forceps includes first and second shafts having a jaw connected thereto. At least one jaw is moveable from an open to a closed position and includes a blade slot extending therealong configured for reciprocation of a blade therethrough. An actuation assembly is disposed within one shaft and is configured for translating the blade between retracted and extended positions. The blade extends at least partially through the blade slot in the extended position. The actuation assembly includes an actuator engaged to a belt disposed within the shaft. The belt is configured for rotation about at least one pulley. A blade holder having the blade connected thereto is engaged to the belt. The blade holder defines a pre-determined load limit that, when exceeded, disengages the blade holder from the belt. Translating the actuator proximally translates the blade distally to the extended position when the blade holder is engaged to the belt.

6 Claims, 5 Drawing Sheets

(56) References Cited

U.S. PATENT DOCUMENTS

| | | | |
|---|---|---|---|
| D457,958 S | 5/2002 | Dycus et al. | |
| D457,959 S | 5/2002 | Tetzlaff et al. | |
| 6,514,252 B2 | 2/2003 | Nezhat et al. | |
| 6,558,385 B1 | 5/2003 | McClurken et al. | |
| 6,685,724 B1 | 2/2004 | Haluck | |
| D493,888 S | 8/2004 | Reschke | |
| D496,997 S | 10/2004 | Dycus et al. | |
| D499,181 S | 11/2004 | Dycus et al. | |
| D509,297 S | 9/2005 | Wells | |
| 6,940,062 B2* | 9/2005 | Kwon et al. | 250/227.14 |
| D525,361 S | 7/2006 | Hushka | |
| D531,311 S | 10/2006 | Guerra et al. | |
| 7,131,970 B2 | 11/2006 | Moses et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,235,089 B1* | 6/2007 | McGuckin, Jr. | 606/167 |
| 7,252,667 B2 | 8/2007 | Moses et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,500,975 B2 | 3/2009 | Cunningham et al. | |
| 7,695,485 B2* | 4/2010 | Whitman et al. | 606/170 |
| 8,241,282 B2* | 8/2012 | Unger et al. | 606/51 |
| 8,366,709 B2* | 2/2013 | Schechter et al. | 606/52 |
| 2005/0119655 A1* | 6/2005 | Moses et al. | 606/51 |
| 2006/0074417 A1 | 4/2006 | Cunningham et al. | |
| 2006/0167452 A1 | 7/2006 | Moses et al. | |
| 2007/0073303 A1* | 3/2007 | Namba | 606/82 |
| 2007/0088356 A1 | 4/2007 | Moses et al. | |
| 2007/0106297 A1 | 5/2007 | Dumbauld et al. | |
| 2008/0033428 A1 | 2/2008 | Artale et al. | |
| 2009/0012520 A1 | 1/2009 | Hixson et al. | |
| 2009/0149854 A1 | 6/2009 | Cunningham et al. | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 20 2007 00931 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/249,263, filed Oct. 10, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/621,056, filed Nov. 18, 2009.
U.S. Appl. No. 12/690,726, filed Jan. 20 2010.
U.S. Appl. No. 12/692,414, filed Jan. 22, 2010.
U.S. Appl. No. 12/692,810, Jan. 25, 2010.
U.S. Appl. No. 12/696,592, filed Jan. 29, 2010.
U.S. Appl. No. 12/696,857, filed Jan. 29, 2010.
U.S. Appl. No. 12/700,856, Feb. 5, 2010.
U.S. Appl. No. 12/710,033, filed Feb. 22, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

(56) References Cited

OTHER PUBLICATIONS

Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.

(56) References Cited

OTHER PUBLICATIONS

Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

\* cited by examiner

SURGICAL FORCEPS INCLUDING BELT BLADE REVERSER MECHANISM

BACKGROUND

The present disclosure relates to a surgical forceps and, more particularly, to a surgical forceps including a belt-like blade reverser mechanism.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal. However, imprecise separation of tissue may result from, for example, misalignment of the blade member with respect to the sealing line. Blade misalignment may also result in blade overload and/or blade fracture, which may pose problems to the user.

SUMMARY

In accordance with the present disclosure, a forceps is provided. The forceps includes first and second shaft members each having a jaw member disposed at a distal end of the respective shaft member. One or both of the jaw members is moveable from an open position to a closed position for grasping tissue between the jaw members. One or both of the jaw members also includes a longitudinally extending blade slot configured for reciprocation of a blade through the blade slot(s). An actuation assembly is disposed within one of the shaft members and is configured for selectively translating the blade between a retracted position and an extended position. The blade extends partially, or entirely, through the blade slot in the extended position. The actuation assembly includes an actuator extending from the shaft member and mechanically engaging a belt. The belt is disposed within the shaft and is configured for rotation about one or more pulleys. A blade holder is mechanically engaged to the belt and includes the blade disposed at a distal end thereof. The blade holder defines a pre-determined load limit such that, when a force on the blade exceeds the pre-determined load limit, the blade holder is disengaged from the belt. Translating the actuator proximally translates the blade distally from the retracted to the extended position (when the blade holder is engaged to the belt).

In one embodiment, the belt includes an actuator mounting portion for engagement of the actuator thereon.

In another embodiment, the belt includes a blade holder mounting portion for engagement of the blade holder thereon. The blade holder mounting portion may define a pre-determined load limit such that when a force on the blade exceeds the pre-determined load limit, the blade holder mounting portion disengages the blade holder from the belt. Translating the actuator proximally no longer translates the blade distally once the blade holder has been disengaged from the belt.

In yet another embodiment, the actuation assembly includes one or more biasing members for biasing the blade in the retracted position. The actuation assembly may also include a return biasing member coupled to the blade holder for returning the blade back to the retracted position once the blade has been deployed In still yet another embodiment, one or more of the pulleys is rotatably mounted within the shaft. Further, the actuation assembly may include two pulleys where each of the pulleys has a different diameter. Alternatively, the two pulleys may define substantially similar diameters.

In another embodiment, the belt is formed partially, or entirely, from an elastic material. More specifically, the belt may be formed from reinforced silicon. The belt may further include a plurality of notches disposed thereon for engaging the actuator and/or the blade holder.

In accordance with another embodiment of the present disclosure, a forceps is provided. The forceps includes first and second shaft members each having a jaw member disposed at a distal end thereof. One (or both) of the jaw members is moveable from an open position to a closed position for grasping tissue therebetween. One (or both) of the jaw members includes a blade slot extending longitudinally therealong that is configured for reciprocation of a blade therethrough. An actuation assembly is disposed within one of the shaft members. The actuation assembly is configured to selectively translate the blade between a retracted position and an extended position. In the extended position, the blade extends at least partially through the blade slot. The actuation assembly includes an actuator extending from the shaft member and mechanically engaged to a belt disposed within the shaft member. The belt is configured for rotation about one (or more) pulleys. A blade holder is mechanically engaged to the belt and has the blade disposed at a distal end thereof. A biasing mechanism is coupled to the actuator to bias the actuator toward a proximal position and the blade toward the retracted position. Translating the actuator proximally translates the blade distally to the extended position.

In one embodiment, the pulley(s) is rotatably mounted within the shaft.

In another embodiment, the belt is formed partially (or entirely) from an elastic material. The belt may be formed from reinforced silicon.

In yet another embodiment, the belt includes a plurality of notches disposed thereon for engaging the actuator and/or the blade holder.

An electrosurgical system is also provided in accordance with the present disclosure. The electrosurgical system includes a generator and a forceps. The forceps includes first and second shaft members each having a jaw member disposed at a distal end thereof. One or both of the jaw members is moveable from an open position to a closed position for grasping tissue therebetween. One or both of the jaw members includes a blade slot extending longitudinally therealong that is configured for reciprocation of a blade therethrough. The first jaw member is connected to the generator for providing a first electrical potential, while the second jaw member is also connected to the generator for providing a second electrical potential. An actuation assembly is disposed within one of the shaft members and is configured for selectively translating the blade between a retracted position and an extended position. In the extended position, the blade extends partially (or entirely) through the blade slot. The actuation assembly includes an actuator extending from the shaft member and mechanically engaging a belt disposed within the shaft. The belt is configured for rotation about one or more pulleys. A blade holder is mechanically engaged to the belt and has the blade disposed at a distal end thereof. The blade holder defines a pre-determined load limit such that, when a force on the blade exceeds the pre-determined load limit, the blade holder is disengaged from the belt. Translating the actuator proximally translates the blade distally to the extended position when the blade holder is engaged to the belt.

BRIEF DESCRIPTION OF THE DRAWINGS

Various embodiments of the subject instrument are described herein with reference to the drawings wherein.

DETAILED DESCRIPTION

Figure 1:
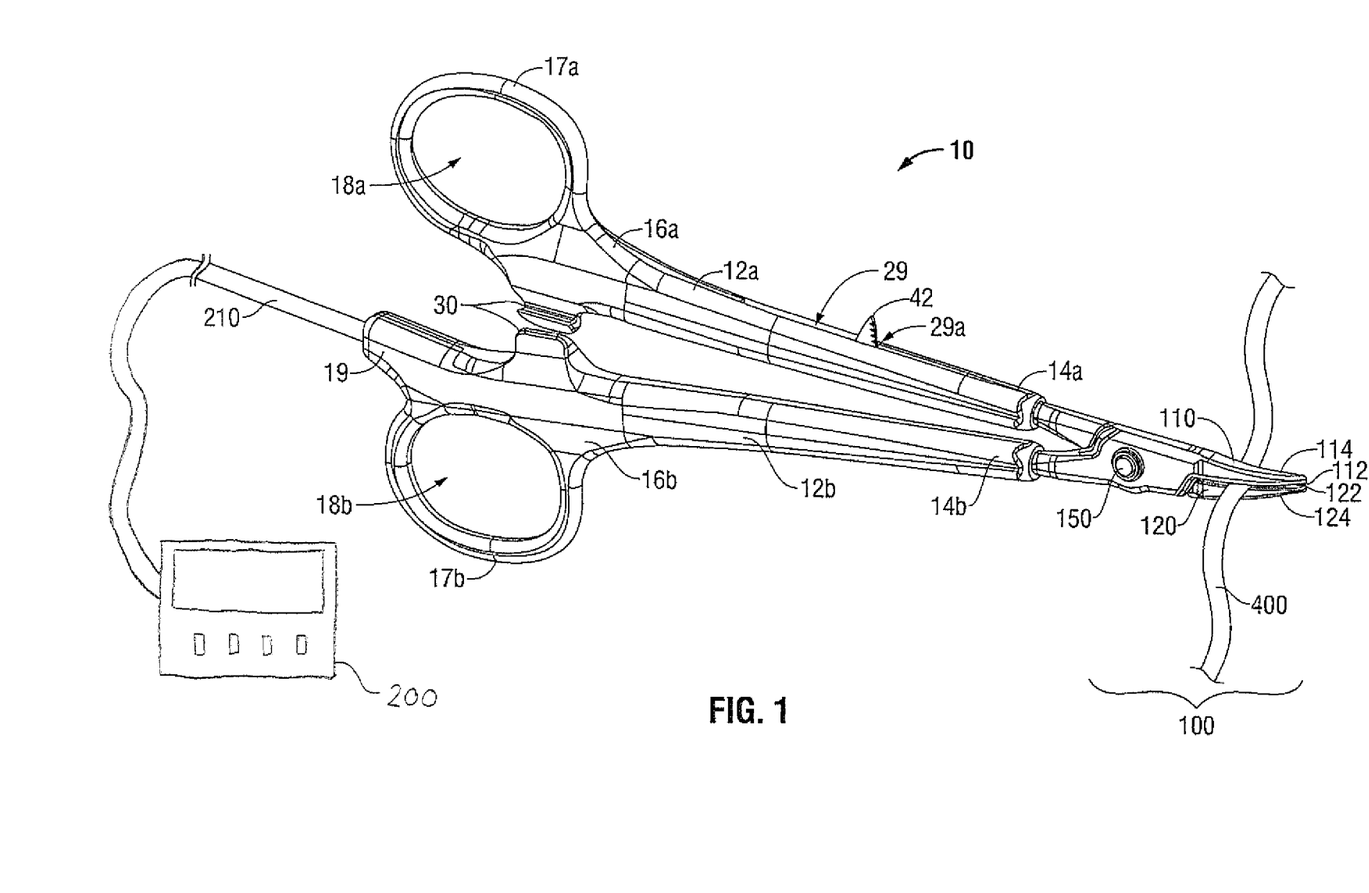
FIG. 1 is a side, perspective view of a forceps according to an embodiment of the present disclosure.

Referring initially to FIG. 1, a forceps 10 includes two elongated shafts 12a and 12b each having a proximal end 16a and 16b and a distal end 14a and 14b, respectively. In the drawings and in the descriptions which follow, the term "proximal," as is traditional, will refer to the end of the forceps 10 that is closer to the user, while the term "distal" will refer to the end that is further from the user.

The forceps 10 includes an end effector assembly 100 attached to distal ends 14a and 14b of shafts 12a and 12b, respectively. As explained in more detail below, the end effector assembly 100 includes a pair of opposing jaw members 110 and 120 that are pivotably connected about a pivot pin 150.

Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots the jaw members 110 and 120 from an open position, wherein the jaw members 110 and 120 are disposed in spaced-apart relation relative to one another to a closed position (FIG. 1), wherein the jaw members 110 and 120 cooperate to grasp tissue 400 therebetween.

A ratchet 30 may be included for selectively locking the jaw members 110 and 120 relative to one another at various positions during pivoting. Ratchet 30 may include graduations or other visual markings that enable the user to easily and quickly ascertain and control the amount of closure force desired between the jaw members 110 and 120.

With continued reference to FIG. 1, one of the shafts, e.g., shaft 12b, includes a proximal shaft connector 19 that is designed to connect the forceps 10 to a source of electrosurgical energy such as an electrosurgical generator 200. Proximal shaft connector 19 secures an electrosurgical cable 210 to the forceps 10 such that the user may selectively apply electrosurgical energy from generator 200 to either (or both) of jaw members 110, 120 as needed.

As mentioned above, the two opposing jaw members 110 and 120 of the end effector assembly 100 are pivotable about pivot pin 150 from the open position to the closed position for grasping tissue 400 therebetween. Jaw member 110 includes an insulated outer housing 114 that is dimensioned to mechanically engage an electrically conductive sealing surface 112 of jaw member 110. Similarly, jaw member 120 includes an insulated outer housing 124 that is dimensioned to mechanically engage an electrically conductive sealing surface 122 of jaw member 120. Electrically conductive sealing surfaces 112 and 122 are opposed to one another, such that, upon activation, electrosurgical energy may be supplied to the electrically conductive sealing surfaces 112 and 122 for sealing tissue 400 disposed between the jaw members 110 and 120. More particularly, a first electrical potential may be provided to first jaw member 110 and a second electrical potential may be provided to second jaw member 120 to conduct energy between the sealing surfaces 112, 122 of jaw members 110, 120, respectively, to seal tissue 400 disposed therebetween.

Figure 3:
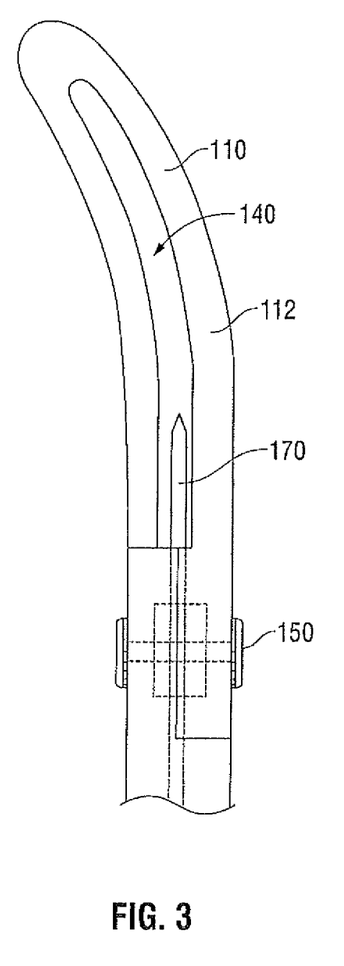
FIG. 3 is a top view of a jaw member of the forceps of FIG. 1.

As best seen in FIG. 3, jaw member 110 includes a blade slot, or blade channel 140 extending therealong. The blade channel 140 is configured for reciprocation of a cutting mechanism, e.g., a blade 170, therethrough. As shown, blade channel 140 is defined completely within jaw member 110. However, blade channel 140 may be formed when two opposing blade channels defined within respective jaw members 110 and 120 come together upon pivoting of the jaw members 110 and 120 to the closed position. Further, the blade channel 140 may be configured to facilitate and/or enhance cutting of tissue during reciprocation of the cutting blade 170 in the distal direction.

Figure 2:
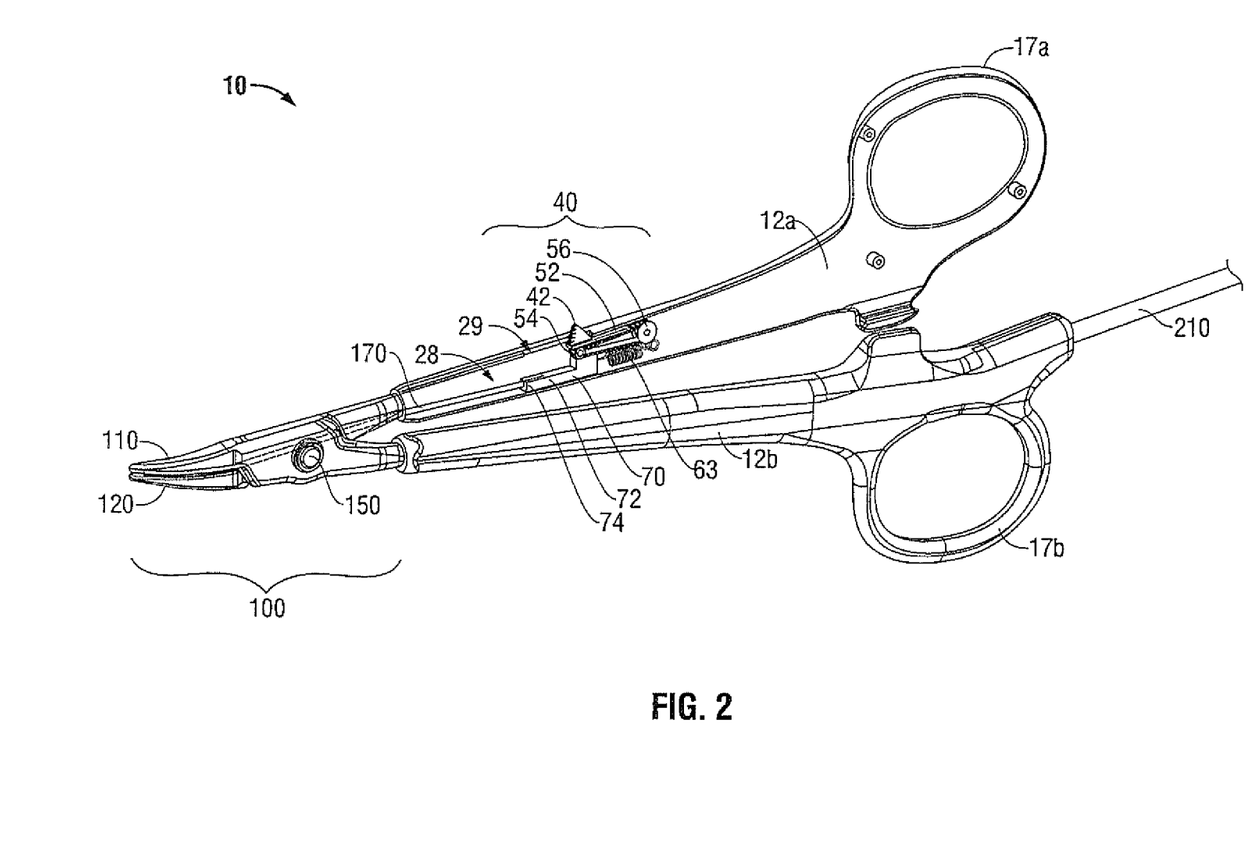
FIG. 2 is a side, perspective view of the forceps of FIG. 1 with a portion of a handle removed to show the internal components therein.

Referring now to FIG. 2, the arrangement of shaft 12a is slightly different from shaft 12b. As shown in FIG. 2, wherein a portion of the housing of shaft 12a has been removed to show the internal components therein, shaft 12a is hollow to define a chamber 28 therethrough that is dimensioned to house an actuation assembly 40 and a blade assembly 70 therein. Blade assembly 70 includes a blade holder 72 having blade 170 disposed at a distal end 74 thereof. Blade 170 may be integral with blade holder 72, or may be attached thereto by other suitable mechanisms, e.g., by a plurality of pins disposed through both blade 170 and blade holder 72, welding, adhesive, etc. As will be described in detail below, blade 170 is translatable through shaft 12a and at least partially into blade channel 140 (FIG. 3) to cut tissue 400 disposed between jaw members 110 and 120.

Figure 4:
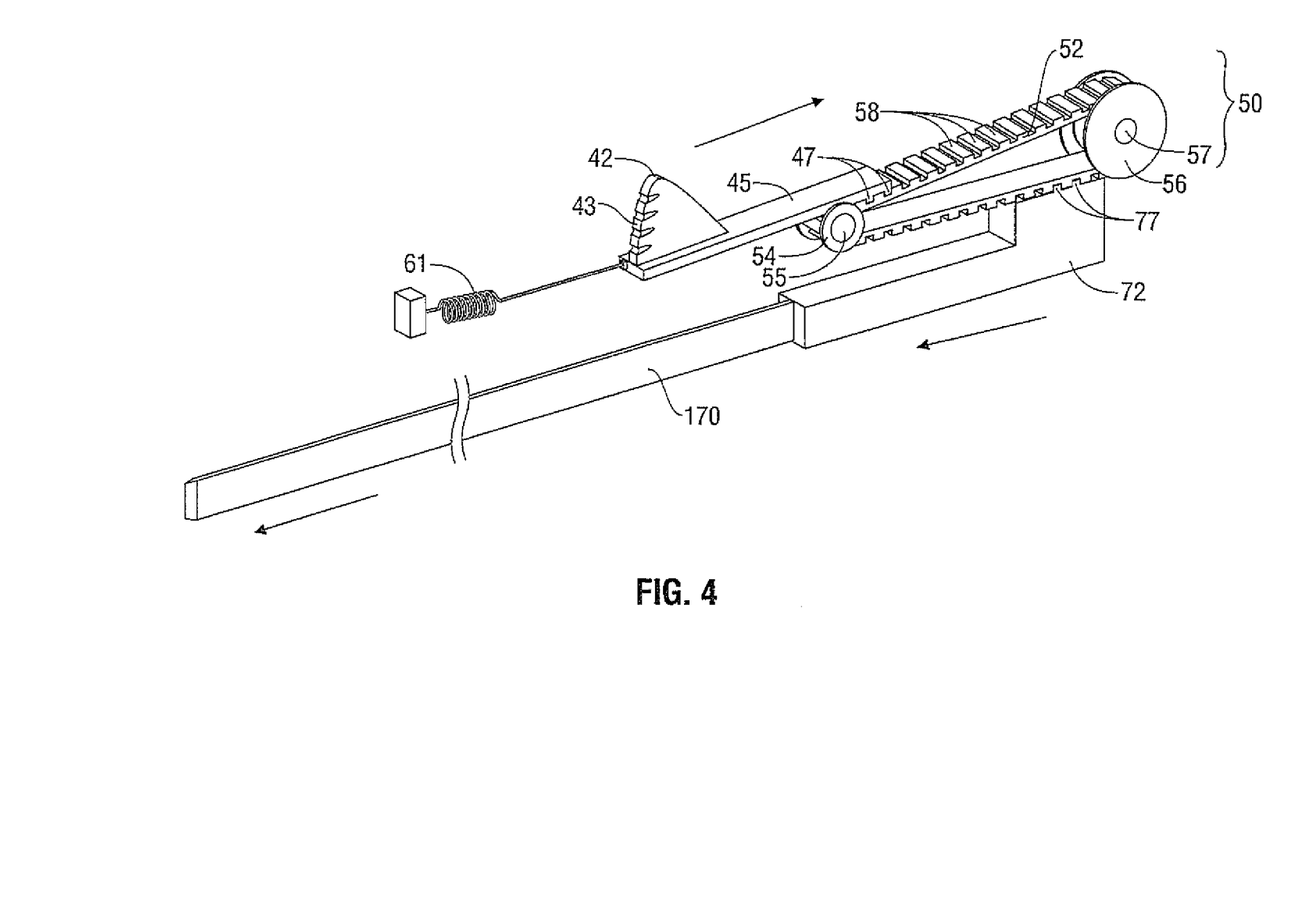
FIG. 4 is a schematic illustration of an actuation assembly of the forceps of FIG. 1, with parts separated.

With reference now to FIGS. 2 and 4, actuation assembly 40 includes an actuator 42 that extends from shaft 12a and is slidable with respect to shaft 12a. A slot 29 is defined within shaft 12a to permit longitudinal translation of actuator 42 with respect to shaft 12a. More specifically, actuator 42 includes a finger tab 43 and a base 45. Finger tab 43 is configured to slide within slot 29 defined within shaft 12a. Finger tab 43 extends from shaft 12a such that a user may selectively translate actuator 42 longitudinally via engaging finger tab 43. Finger tab 43 may include one or more ergonomically friendly features that enhance the tactile feel and grip for the user to facilitate proximal translation of the actuator. The base 45 of actuator 42 is disposed within chamber 28 of shaft 12a.

Referring now to the embodiment of FIG. 4, actuation assembly 40 further includes a belt and pulley system 50 disposed within chamber 28 of shaft 12a. Although a two pulley system 50 is shown in the Figures, single or multiple (e.g., more than two) pulley systems may also be provided. Pulleys 54 and 56 are positioned within chamber 28 of shaft 12a and are rotatably mounted therein via pins 55 and 57, respectively. Belt 52 is positioned about pulleys 54 and 56 and is rotatable about pulleys 54 and 56. As shown in FIG. 4, actuator 42 may be mounted to belt 52 via the engagement of notches 58 defined within belt 52 and complementary-shaped notches 47 defined within base 45 of actuator 42. Similarly, blade holder 72 may be attached to belt 52 via the engagement of notches 58 with corresponding notches 77 of blade holder 72.

As can be appreciated, due to the configuration of actuator 42 and blade holder 72 being disposed on opposite portions of belt 52 with pulleys 54 and 56 therebetween, proximal translation of actuator 42 causes counter-clockwise rotation of belt 52 about pulleys 54 and 56 and, thus, distal translation of blade holder 72. Accordingly, actuator 42 may be translated proximally to move blade 170 between a retracted position and an extended position wherein blade 170 extends into blade channel 140 when in the extended position to cut tissue 400 disposed between the jaw members 110 and 120.

Referring now to FIGS. 1 and 4, actuator 42 is initially disposed in a distal position, wherein finger tab 43 is positioned at a distal end 29a of slot 29 of shaft 12a. At the same time, blade holder 72 is disposed in a proximal position such that blade 170 is disposed completely within shaft 12a and does not extend into blade channel 140 defined by jaw members 110 and 120. A biasing mechanism 61, e.g., a spring 61, coupled to actuator 42 may bias actuator 42 in the distal position such that blade holder 72 is biased in the proximal, or retracted position. Further, a return spring 63 (FIG. 2), or other biasing mechanism 63, may be coupled to blade holder 72 to similarly bias blade holder 72 in the retracted position and bias actuator 42 in the distal position. Return spring 63 also acts to return blade holder 72, and thus blade 170, to the retracted position once blade 170 has been deployed. Therefore, a user must overcome the biasing force of the biasing spring 61 and/or return spring 63 in order to translate the actuator 42 proximally to advance the blade 170 distally through blade channels 140a, 140b defined within jaw members 110 and 120. Similarly, when the proximal force applied to finger tab 43 is removed, e.g., when actuator 42 is released, blade 170 is returned to the retracted position under the bias of return spring 63 (FIG. 2). This configuration acts as a safety feature that helps prevents blade 170 from being inadvertently extended and/or retained in the extended position.

Figure 5:
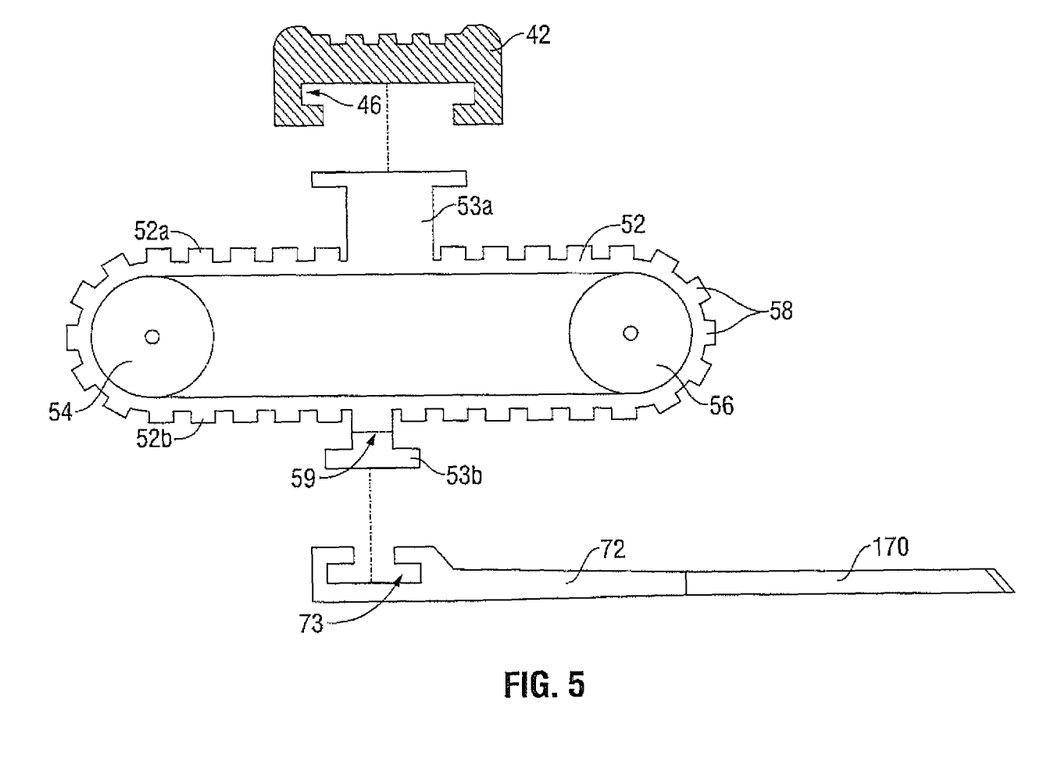
FIG. 5 is a schematic illustration of another embodiment of an actuation assembly of the forceps of FIG. 1.

In the embodiment of FIG. 5, belt 52 may include an actuator mounting portion 53a, that is disposed on a first portion 52a of belt 52. Actuator mounting portion 53a may be injection molded to belt 52 or may be attached thereon in any other suitable fashion. Actuator mounting portion 53a is shown having a generally "T"-shaped configuration. Recessed portion 46 of base 45 of actuator 42 is shown having a generally "T"-shaped configuration, complementary to the "T"-shaped actuator mounting portion 53a of belt 52. However, actuator mounting portion 53a may be shaped complementarily to recessed portion 46 of actuator 42 in a variety of different configurations.

With continued reference to FIG. 5, actuation assembly 40 further includes a blade holder mounting portion 53b disposed on a second, opposing portion 52b of belt 52. Similar to actuator mounting portion 53a, blade holder mounting portion 53b may be injection molded to belt 52 or may be attached thereon in any other suitable fashion. As will be described in more detail below, blade holder mounting portion 53b may further include a predictive shear feature 59 defining a pre-determined load limit. Blade holder mounting portion 53b is shown having a generally "T"-shaped configuration. Blade holder 72 may include a recessed portion 73 (FIG. 5) configured for engaging blade holder mounting portion. Recessed portion 73 of blade holder 72 may define a complementary "T"-shaped configuration or any other shape complementary to the shape of blade holder mounting portion 53b such that blade holder 72 may be attached to belt 52.

In the configuration shown in FIG. 5, pulley 54 and pulley 56 have a substantially similar diameter such that translation of actuator 42 proximally translates blade holder 72 distally in a substantially parallel direction. However, it is also envisioned that pulley 54 and pulley 56 may have different diameters, e.g., as shown in FIG. 4, where pulley 56 has a diameter that is larger than a diameter of pulley 54, such that actuator 42 is translated proximally at a pre-determined angle with respect to the distal translation of blade holder 72.

In either of the above embodiments, belt 52 may be made from surgical-grade silicon. Alternatively, belt 52 may be made from any other suitable material having similar durability and flexibility as surgical-grade silicon. Belt 52 may also be reinforced, e.g., with a plurality of fibers (not shown) disposed therethrough, to limit the flexibility and/or increase durability and rigidity of belt 52. A durable and rigid belt 52 helps ensure proper alignment and translation of the blade 170 through the blade channel 140. On the other hand, a flexible belt 52 helps protect the blade 170 from excessive loading and/or fracture. In other words, belt 52 must be durable and rigid enough such that blade 170 may pass consistently and accurately from the retracted to the extended position but must also be flexible, allowing belt 52 to flex in response to an increased load on the blade 170, thereby helping to prevent blade fracture.

Further, belt 52, and the other components of actuation assembly 40 and forceps 10, may be made from EtO compatible material, such that forceps 10 may be sterilizable for repeated use via EtO gas sterilization or other similar methods. Alternatively, forceps 10 may be configured as a disposable device such that forceps 10 may be discarded after a single use.

In other embodiments, belt 52 may be a linked chain, e.g., a roller chain (not shown), configured to rotate about geared pulleys. In such an embodiment, the actuator mounting portion 53a (FIG. 5) and blade holder mounting portion 53b (FIG. 5) may be mechanically engaged, or otherwise attached to the roller chain. Other configurations of belt 52 are also possible.

With reference now to FIGS. 1 and 5, when a user translates the actuator 42 proximally to advance the blade 170 through tissue 400 disposed between the jaw members 110 and 120, specific portions of tissue 400 may resist the blade 170 more than others. In other words, the force required to urge blade 170 through blade channel 140 may vary depending on the composition and/or size of tissue 400 to be cut. As the user translates the actuator 42 proximally, blade 170 is urged into tissue 400 and tissue 400 resists translation of blade 170 therethrough. This resistance imparts a load on blade 170. If the load is great enough, the blade 170 may fracture. Providing a belt 52 with at least some elasticity, e.g., a belt 52 made from reinforced surgical silicon, helps prevent such an occurrence.

Additionally, as shown in FIG. 5, a predictive shear feature 59 may be included within blade holder engaging portion 53b of belt 52 to further limit blade overload and/or blade fracture. More specifically, the blade holder engaging portion 53b may define a pre-determined load limit. During actuation, as tissue 400 resists distal translation of blade 170, and as belt 52 urges blade holder 72 distally, the load is applied to the blade holder engaging portion 53b as well as to the blade 170. A pre-determined load limit built into the blade holder engaging portion 53b would cause the blade holder engaging portion 53b to shear in response to a load exceeding the pre-determined limit, thereby disengaging the blade holder 72 from the belt 52. Accordingly, instead of blade 170 being urged into tissue 400 to the point of fracture, the blade 170 would be disengaged from belt 52 such that translation of actuator 42 no longer affects translation of blade 170 through tissue 400, thereby removing the load from blade 170 and helping to prevent blade fracture. The pre-determined load limit may correspond to a load below the blade fracture point. In other words, the pre-determined load limit would disengage the blade holder 72 from the belt 52 prior to blade fracture. Further, the return spring 63, in conjunction with the predictive shear feature 69 would help ensure that, in the event of blade fracture and/or disengagement from belt 52, blade 170 and any corresponding debris would remain inside the shaft 28, and would not compromise the surgical site. Alternatively, actuator engaging portion 53a of belt 52 may be configured with a similar feature (not explicitly shown) such that actuator 42, rather than blade holder 72, would be disengaged from belt 52 upon exceeding the pre-determined load limit on the blade 170.

Forceps 10 may also include a lockout mechanism (not shown) for preventing accidental reciprocation of blade 170 through blade channel 140. Such a feature would prevent blade 170 from being translated distally until the jaw members 110 and 120 are disposed in the closed position. The lockout mechanism may include mechanical components and/or electrical components, such as a sensor (not shown).

With reference now to FIGS. 1-5, the operation of forceps 10 will now be described. Initially, forceps 10 is positioned such that jaw members 110 and 120 are spaced-apart relative to one another with tissue 400 disposed therebetween. At this point, the lockout mechanism may be used to prevent inadvertent deployment of blade 170 until jaw members 110 and 120 are moved to the closed position. Once positioned as desired, a user may engage finger holes 18a and 18b to squeeze shafts 12a and 12b together, such that jaw members 110 and 120 are moved from the spaced-apart to the closed position, grasping tissue 400 therebetween. As discussed above, ratchet 30 may selectively lock the jaw members 110 and 120 relative to one another at various positions during pivoting, such that the desired force may be applied accurately and consistently to tissue 400. The user may then selectively apply electrosurgical energy to electrically conductive sealing plates 112 and 122 of jaw members 110 and 120, respectively, to thereby effectuate a tissue seal. Once tissue 400 has been adequately sealed, the user may translate actuator 42 proximally, thereby rotating belt 52 about pulleys 54 and 56 and advancing blade 170 distally through blade channel 140 defined within jaw members 110 and 120 to cut tissue 400 therebetween. When blade 170 has been advanced sufficiently through blade channel 140 to cut tissue 400 disposed between jaw members 110 and 120, actuator 42 may be released by the user. Actuator 42 will then return to the initial, distal position, while blade 170 returns to the initial proximal position under the bias of biasing spring 61 and/or return spring 63. Once tissue 400 has been sealed and cut, the user may move finger holes 18a and 18b apart from one another to open jaw members 110 and 120 such that the forceps 10 may be removed from the surgical site.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   first and second shaft members each having a jaw member disposed at a distal end thereof, at least one of the jaw members moveable relative to the other from an open position to a closed position for grasping tissue therebetween;
   a blade selectively translatable relative to the jaw members between a retracted position and an extended position wherein the blade extends at least partially between the jaw members, the blade defining a first pre-determined load limit; and
   an actuation assembly coupled to one of the shaft members, the actuation assembly including:
      at least one pulley disposed within the shaft member;
      a belt disposed about the at least one pulley and configured for rotation about the at least one pulley, the belt including an integral blade holder mounting portion defining a second pre-determined load limit less than the first pre-determined load limit;
      an actuator extending from the shaft member and engaged to the belt;
      a blade holder mechanically engaged to the blade holder mounting portion of the belt and having the blade disposed at a distal end thereof such that translating the actuator proximally translates the blade distally towards the extended position, wherein, in response to a force on the blade that exceeds the second pre-determined load limit, the blade holder mounting portion is separated from the belt to disengage the blade holder from the belt; and
      a return biasing member configured to bias the blade towards the retracted position, the return biasing member operably coupled between the blade holder and the shaft member such that the return biasing member remains operable to bias the blade towards the retracted position after disengagement of the blade holder from the belt.

2. The forceps according to claim 1, wherein the belt includes an actuator mounting portion for engagement of the actuator thereon.

3. The forceps according to claim 1, wherein the at least one pulley is rotatably mounted within the shaft.

4. The forceps according to claim 1, wherein the belt is formed at least partially from an elastic material.

5. The forceps according to claim 1, wherein the belt is formed from reinforced silicon.

6. The forceps according to claim 1, wherein the actuation assembly includes two pulleys, each pulley having a different diameter.

* * * * *